(12) United States Patent
Merkel et al.

(10) Patent No.: US 9,181,151 B2
(45) Date of Patent: Nov. 10, 2015

(54) PROCESS TO MANUFACTURE 2-CHLORO-1,1,1,2-TETRAFLUOROPROPANE (HCFC-244BB)

(71) Applicant: HONEYWELL INTERNATIONAL INC., Morristown, NJ (US)

(72) Inventors: Daniel C. Merkel, Orchard Park, NY (US); Stephen A. Cottrell, Baton Rouge, LA (US); Robert C. Johnson, Lancaster, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/021,256

(22) Filed: Sep. 9, 2013

(65) Prior Publication Data

US 2014/0012047 A1    Jan. 9, 2014

Related U.S. Application Data

(63) Continuation of application No. 12/512,955, filed on Jul. 30, 2009, now Pat. No. 8,664,455.

(60) Provisional application No. 61/087,206, filed on Aug. 8, 2008.

(51) Int. Cl.
| | |
|---|---|
| *C07C 17/25* | (2006.01) |
| *C07C 19/08* | (2006.01) |
| *C07C 21/18* | (2006.01) |
| *C07C 17/087* | (2006.01) |
| *C07C 17/20* | (2006.01) |
| *C07C 19/10* | (2006.01) |

(52) U.S. Cl.
CPC ............ *C07C 17/087* (2013.01); *C07C 17/206* (2013.01); *C07C 17/25* (2013.01); *C07C 19/10* (2013.01); *C07C 21/18* (2013.01)

(58) Field of Classification Search
CPC combination set(s) only.
See application file for complete search history.

(56) References Cited

U.S. PATENT DOCUMENTS

| | | | |
|---|---|---|---|
| 2,931,840 A | 4/1960 | Marquis | |
| 4,900,874 A | 2/1990 | Ihara et al. | |
| 5,571,770 A | 11/1996 | Kim et al. | |
| 6,362,383 B1 | 3/2002 | Wilmet et al. | |
| 6,903,063 B2 | 6/2005 | Pham et al. | |
| 7,345,209 B2 | 3/2008 | Mukhopadhyay et al. | |
| 8,084,653 B2 | 12/2011 | Tung et al. | |
| 8,664,455 B2 * | 3/2014 | Merkel et al. | 570/156 |
| 8,916,733 B2 * | 12/2014 | Merkel et al. | 570/167 |
| 2005/0020862 A1 | 1/2005 | Tung et al. | |
| 2007/0007488 A1 | 1/2007 | Singh et al. | |
| 2007/0197842 A1 | 8/2007 | Mukhopadhyay et al. | |
| 2009/0030244 A1 | 1/2009 | Merkel et al. | |
| 2009/0030247 A1 | 1/2009 | Johnson et al. | |
| 2009/0043136 A1 | 2/2009 | Wang et al. | |
| 2009/0182179 A1 | 7/2009 | Merkel et al. | |
| 2009/0227822 A1 | 9/2009 | Pham et al. | |
| 2009/0256110 A1 | 10/2009 | Merkel et al. | |
| 2009/0312585 A1 | 12/2009 | Merkel et al. | |
| 2010/0048961 A1 | 2/2010 | Merkel et al. | |

FOREIGN PATENT DOCUMENTS

| | | |
|---|---|---|
| EP | 0328148 A1 | 8/1989 |
| EP | 939071 B1 | 7/2003 |
| WO | 9218242 A1 | 10/1992 |
| WO | 2007079431 A2 | 7/2007 |
| WO | 2009/003084 A1 | 12/2008 |
| WO | 2009026526 A1 | 2/2009 |
| WO | 2012009114 A3 | 1/2012 |

OTHER PUBLICATIONS

D. Yuansheng, et al., "Preparation and Application of 3,3,3-trifluoropropene", Zhejiang Chemical Industry (2004) vol. 35(4), pp. 3-4.

* cited by examiner

*Primary Examiner* — Clinton Brooks
(74) *Attorney, Agent, or Firm* — Bruce O. Bradford

(57) ABSTRACT

The invention provides an improved process to manufacture 2-chloro-1,1,1,2-tetrafluoropropane (HCFC-244bb) by reacting 2-chloro-3,3,3,-trifluoropropene (HCFO-1233xf) with hydrogen fluoride, in a liquid phase reaction in the presence of hydrogen chloride and a liquid phase fluorination catalyst. The hydrogen chloride is added into the reaction from an external source at a pressure of about 100 psig or more. The HCFC-244bb is an intermediate in the production of 2,3,3,3-tetrafluoropropene-1 (HFO-1234yf).

8 Claims, No Drawings

PROCESS TO MANUFACTURE 2-CHLORO-1,1,1,2-TETRAFLUOROPROPANE (HCFC-244BB)

CROSS REFERENCE TO RELATED APPLICATION

This application is a continuation of U.S. application Ser. No. 12/512,955 filed on Jul. 30, 2009 (currently pending), which claims the priority benefit of U.S. Provisional Patent Application Ser. No. 61/087,206 filed Aug. 8, 2008, which is incorporated herein by reference.

BACKGROUND OF THE INVENTION

1. Field of the Invention

The present invention relates to an improved process for manufacturing 2-chloro-1,1,1,2-tetrafluoropropane (HCFC-244bb), or more particularly to an improved process for the production of HCFC-244bb by reacting 2-chloro-3,3,3,-trifluoropropene (HCFO-1233xf) with hydrogen fluoride, in a liquid phase reaction vessel in the presence of hydrogen chloride and a liquid phase fluorination catalyst. The HCFC-244bb is an intermediate in the production of 2,3,3,3-tetrafluoropropene (HFO-1234yf) which is a refrigerant with low global warming potential.

2. Description of the Related Art

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above. Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). HFO-1234yf has been found to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid. Thus, there is a need for new manufacturing processes for the production of tetrafluoropropenes and in particular 2,3,3,3-tetrafluoropropene.

In U.S. Pat. No. 2,931,840, methyl chloride has been pyrolyzed along with $CF_2HCl$ at 800° C. to give a product stream that contains about 15% of $CF_3CF=CH_2$. HFO-1234yf has also been made by the dehydrofluorination of $CF_3CHFCH_2F$ with KOH in butyl ether (Chem. Abstr. 1961: 3490, and by the reaction of $CF_3CF_2CH_2OH$ with hydrogen in U.S. Pat. No. 4,900,874.

It would be advantageous to have a process for the manufacture of HFO-1234yf that is continuous, and which uses readily available raw materials. As the prior art processes fail in one or more of these desirable features, more advantageous routes are desired, especially those amenable to large-scale manufacture. One of the steps in recent manufacturing processes for HFO-1234yf requires the fluorination HCFO-1233xf with hydrogen fluoride to form 2-chloro-1,1,1-tetrafluoropropane (HCFC-244bb). In the liquid phase fluorination of HCFO-1233xf to produce HCFC-244bb, no HCl is produced because the reaction is strictly a hydrofluorination reaction where HF adds across the double bond. This lack of HCl by-product formation is unique when compared to other well-known liquid phase fluorination reactions that produce CFCs (e.g. CFC-12), HCFCs (e.g. HCFC-22, HCFC-142b), and HFCs (e.g. HFC-143a, HFC-245fa). This is because these reactions involve a halogen exchange, in whole or in part. That is, $F^-$ replaces a $Cl^-$ on the molecule. It is advantages to run liquid phase fluorination reactions at relatively elevated pressures which are easily achieved by the formation of HCl. Because it is non-condensable at the desired reaction conditions, HCl formation also increases mixing in the reactor and it readily comes out in the overhead of the catalyst stripper and helps by carrying out the fluorinated product. Because no HCl is produced in the reaction of HCFO-1233xf to HCFC-244bb there is less mixing in the reactor which may decrease conversion and promote by-product formation. In addition, the reactor is more difficult to control because there is no HCl to create high pressure nor to help carry out the HCFC-244bb that is formed.

In the present invention HCl is co-fed to the reactor along with the HF and HCFO-1233xf. The reactor and catalyst stripper runs like a typical liquid phase fluorination reaction that produce CFCs, HCFC's, and HFCs as described above. This has a number of benefits. It enables the reaction to achieve and run at relatively elevated pressures, it increases mixing in the reactor, and it readily leaves the reactor in the overhead of the catalyst stripper carrying with it product HCFC-244bb. The HCl co-feed is essentially inert, does not participate in the fluorination reaction, and produces little or no unwanted by-products. Any source of HCl can be used in the reaction. Preferably HCl produced in-situ from a prior step in a multi-step process to produce HFO-1234yf is used as the source. An example of such a step involves the fluorination of 1, 1,2,3-tetrachloropropene or 1,1,1,2,3-pentachloropropane with HF, optionally but preferably in the presence of a fluorination catalyst to form HCFO-1233xf intermediate and HCl. Then, all or only a portion of the HCl produced in this step is co-fed into the liquid phase fluorination reactor that produces HCFC-244bb.

SUMMARY OF THE INVENTION

The invention provides a process for the production of 2-chloro-1,1,1,2-tetrafluoropropane which comprises reacting 2-chloro-3,3,3,-trifluoropropene with hydrogen fluoride, in a liquid phase reaction vessel in the presence of hydrogen chloride and a liquid phase fluorination catalyst, wherein the hydrogen chloride is added into the reaction from an external source at a pressure of about 100 psig or more.

The invention also provides a process for the production of 2,3,3,3-tetrafluoropropene which comprises (i) continuously reacting 2-chloro-3,3,3,-trifluoropropene with hydrogen fluoride, in a liquid phase reaction and co-feeding hydrogen chloride, in the presence of a liquid phase fluorination catalyst to produce a composition comprising 2-chloro-1,1,1,2-tetrafluoropropane, wherein the hydrogen chloride is added into the reaction from an external source at a pressure of about 100 psig or more; and then (ii) dehydrohalogenating the 2-chloro-1,1,1,2-tetrafluoropropane under conditions effective to produce 2,3,3,3-tetrafluoropropene.

The invention also provides a process for the production of 2,3,3,3-tetrafluoropropene which comprises a) fluorinating 1,1,2,3-tetrachloropropene to produce 2-chloro-3,3,3,-trifluoropropene;

b) reacting the 2-chloro-3,3,3,-trifluoropropene with hydrogen fluoride, in a liquid phase reaction and co-feeding hydrogen chloride, in the presence of a liquid phase fluorination catalyst to produce a composition comprising 2-chloro-1,1,1,2-tetrafluoropropane, wherein the hydrogen chloride is added into the reaction from an external source at a pressure of about 100 psig or more; and then c) dehydrohalogenating the 2-chloro-1,1,1,2-tetrafluoropropane under conditions effective to produce 2,3,3,3-tetrafluoropropene.

DESCRIPTION OF THE INVENTION

The first step in the process for the production of 2-chloro-1,1,1,2-tetrafluoropropane (HCFC-244bb) requires reacting 2-chloro-3,3,3,-trifluoropropene (HCFO-1233xf) with hydrogen fluoride, in a liquid phase reaction vessel in the presence of hydrogen chloride and a liquid phase fluorination catalyst to thereby produce HCFC-244bb. Preferably the reaction is conducted continuously.

HCFO-1233xf is an intermediate in the production of 2,3,3,3-tetrafluoropropene (HFO-1234yf) which is well known in the art as described in U.S. Applications 20070007488 and 20070197842, the specifications of which are incorporated herein by reference. In a method of preparing HCFO-1233xf, precursor reagents are fluorinated with hydrogen fluoride. This may be done, for example, by the gas or liquid phase catalytic fluorination of $CCl_2=CClCH_2Cl$ with HF to yield HCFO-1233xf. The reaction products of such precursors include HCFO-1233xf, unreacted HF, HCl, and other by-products which are then available for separation into component parts.

In the practice of the present invention, a liquid phase catalyst as described below is charged into a fluorination reactor prior to heating the reactor. Any reactor suitable for a fluorination reaction may be used in the invention. Preferably the reactor is constructed from materials which are resistant to the corrosive effects of HF such as Hastelloy-C, Inconel, Monel and fluoropolymer-lined vessels. Such liquid phase fluorination reactors are well known in the art. Then the HF, HCl and the HCFO-1233xf are fed to the reactor after the reactor reaches the desired temperature. In the preferred embodiment, the reaction is conducted at a temperature of from about 30° C. to about 200° C., more preferably from about from about 50° C. to about 150° C., and still more preferably from about 75° C. to about 125° C. The pressure of the reaction varies depending on the temperature, quantity of hydrogen chloride and hydrogen fluoride used, and conversion of HCFO-1233xf. Convenient operating pressure ranges from about 5 psia to about 200 psia, and preferably from 30 to about 175 psia, and most preferably about 60 psia to about 150 psia.

In the preferred embodiment, the catalyst is present in an amount of from about 2% to about 80%, and preferably from about 5% to about 50%, and most preferably from about 10% to about 20%, based on the mole percent of HCFO-1233xf. Fluorination catalysts having a purity of at least 98% are preferred.

Based on reaction stoichiometry, the required mole ratio of HF to HCFO-1233xf is at least equal to the number of double bonds in the starting organic material and preferably is present in an excess. In the preferred embodiment, the mole ratio of HF to HCFO-1233xf ranges from at least about 1:1 to about 50:1, more preferably from about 1:1 to about 30:1 and most preferably from about 2:1 to about 15:1. Any water in the HF will react with and deactivate the catalyst. Therefore substantially anhydrous HF is preferred. By "substantially anhydrous" is meant that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from Honeywell International Inc. of Morristown, N.J.

The liquid phase fluorination reaction is conducted with a sufficient amount of hydrogen chloride to elevate the pressure in the reactor, above the pressure achieved compared to a similar liquid phase reaction without adding hydrogen chloride. In the preferred embodiment, the mole ratio of HCl to HCFO-1233xf ranges from about 0.1:1 to about 10:1, more preferably from about 1:1 to about 5:1 and most preferably from about 1:1 to about 3:1. The hydrogen chloride is added into the reaction from an external source at a pressure of about 100 psig or more; preferably from about 100 psig to about 500 psig, and more preferably from about 120 psig to about 300 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, $CrF_3$, Cr2O3, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, a fluorinated species of $Cr_2O_3$, or combinations thereof. Liquid phase fluorination catalyst comprises $SbCl_5$, $SbCl_3$, $SbF_5$, $SnCl_4$, $TaCl_5$, $TiCl_4$, $NbCl_5$, $MoCl_6$, $FeCl_3$, $CrF_3$, Cr2O3, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, a fluorinated species of $Cr_2O_3$, or combinations thereof.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

The resulting HCFC-244bb, as well as HF and HCl may be recovered from the reaction mixture via any separation or purification method known in the art such as neutralization and distillation. The HCFC-244bb can be used in pure form, or optionally in partially pure form or impure form with the entire effluent from the HCFC-244bb production step used as an intermediate in the production of 2,3,3,3-tetrafluoropropene HFO-1234yf. The process of the invention may be carried out either in a batch or continuous mode. In a continuous process, the HCFO-1233xf, HCl and HF are preferably fed simultaneously to the reactor after the reactor reaches the desired temperature. The temperature and pressure of the fluorination reaction remain essentially the same for both the batch and continuous modes of operation. The residence time or contact time, varies from about 1 second to about 2 hours, preferably from about 5 seconds to about 1 hour and most preferably from about 10 seconds to about 30 minutes. A sufficient quantity of catalyst must be present to effect the fluorination in the residence times described above. In a continuous mode of operation, HF, HCFC-244bb and hydrogen chloride are continuously removed from the reactor.

In a preferred embodiment, the invention relates to a multistep process in which the above described process to produce HCFC-244bb is immediately preceded by a prior process step for producing 2-chloro-3,3,3,-trifluoropropene (HCFO-1233xf) by vapor phase fluorination of 1,1,2,3,-tetrachloropropene (HCC-1230xa) or 1,1,1,2,3-tetrachloropropane (HCC-240db) with hydrogen fluoride to produce a stream comprising hydrogen fluoride, 2-chloro-3,3,3,-trifluoropropene, and hydrogen chloride. Preferably all, and more preferably at least a part of this stream is directly fed to the liquid phase reaction to make HCFC-244bb.

This reaction may be conducted in any reactor suitable for a vapor or liquid phase fluorination reaction. Preferably the reactor is constructed from materials which are resistant to the corrosive effects of hydrogen fluoride and catalyst such as Hastalloy, Inconel, Monel and vessels lined with fluoropolymers. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The reactor is preheated to the fluorination reaction temperature while anhydrous HF is fed to the reactor. The 1,1,2,3,-tetrachloropropene (HCC-1230xa) or 1,1,1,2,3-tetrachloropropane (HCC-240db) and HF may be fed to the reactor at any convenient temperature and pressure. In a preferred embodiment either or both of the HCC-1230xa or HCC-240db and the HF are pre-vaporized or preheated to a temperature of from about 30° C. to about 300° C. prior to entering the reactor. In another embodiment, the HCC-1230xa or HCC-240db and HF are vaporized in the reactor. The HF and HCC-1230xa or HCC-240db feeds are then adjusted to the desired mole ratio. The HF to HCC-1230xa or HCC-240db mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr (0.0966 psig) to about 760 torr (14.69 psig). During the vapor phase fluorination reaction, HCC-1230xa or HCC-240db and HF are reacted in a vapor phase in the presence of the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as using an oxidizing agent such as $O_2$ or chlorine. For example, passing air or air diluted with nitrogen over the catalyst at temperatures of from about 100° C. to about 400° C., preferably from about 200° C. to about 375° C., for from about 8 hours to about 3 days, depending on the size of the reactor.

In one embodiment, the HCFO-1233xf may be recovered from the fluorination reaction product mixture comprised of unreacted starting materials, by-products including HCl, HF, and the HCFO-1233xf by any means known in the art, such as by distillation. For example, the distillation may be preferably conducted in a standard distillation column at a pressure which is less than about 300 psig, preferably less than about 200 psig and most preferably less than 150 psig. The pressure of the distillation column inherently determines the distillation operating temperature. HCl may be recovered by operating the distillation column at from about −40° C. to about 25° C., preferably from about −40° C. to about −20° C. HCFO-1233xf may be recovered by operating the distillation column at from about −10° C. to about 60° C. Single or multiple distillation columns may be used. The distillate portion includes substantially all the HCl, and HCFO-1233xf produced in the reaction and the bottoms portion includes the HF and other impurities.

However, in a more preferred embodiment, the product stream from this step comprising HCFO-1233xf, HCl and HF is fed from the vapor phase fluorination reaction directly into the liquid phase reaction described above, which converts the HCFO-1233xf into the HCFC-244bb.

In another embodiment, the HCFC-244bb produced is then dehydrohalogenated under conditions effective to produce 2,3,3,3-tetrafluoropropene (HFO-1234yf). Preferably the dehydrohalogenating step comprises a gas or vapor phase catalytic reaction.

The catalytic conversion of HCFC-244bb is conducted under conditions effective to dehydrochlorinate HCFC-244bb to produce 2,3,3,3-tetrafluoropropene (HFO-1234yf. Preferably dehydrochlorination of HCFC-244bb is done in a vapor phase, and more preferably in a fixed-bed reactor in the vapor phase. The dehydrohalogenation reaction may be conducted in any suitable reaction vessel or reactor, but it should preferably be constructed from materials which are resistant to the corrosive effects of hydrogen chloride (to the extent that such material is formed under the dehydrohalogenation conditions) such as nickel and its alloys, including Hastelloy, Inconel, Incoloy, and Monel or vessels lined with fluoropolymers and may employ single or multiple tubes packed with a dehydrohalogenation catalyst.

Catalysts for HCFC-244bb Dehydrochlorination to HFO-1234yf.

The catalysts may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

The HCFC-244bb is introduced into the reactor either in pure form, partially purified form, or as part of the reactor effluent from the preceding step. The HCFC-244bb may optionally be fed with an inert gas diluent such as nitrogen, argon, or the like. In a preferred embodiment of the invention, the HCFC-244bb is pre-vaporized or preheated prior to entering the reactor. Alternately, the HCFC-244bb is vaporized inside the reactor. Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psig) to about 760 torr (14.69 psig). Contact time of the HCFC-244bb with the catalyst may range from about 0.5 seconds to about 120 seconds, however, longer or shorter times can be used.

Preferably in such dehydrofluorination embodiments as described in this section, the conversion of the HCFC-244bb is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art such as using an oxidizing agent such as $O_2$ or chlorine. For example, by passing air or air diluted with nitrogen over the catalyst at temperatures of from about 100° C. to about 400° C., preferably from about 200° C. to about 375° C., for from about 0.5 hour to about 3 days depending on the size of the reactor.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC-244bb. Some portion or substantially all of these components of the reaction product may be recovered from the reaction mixture via any separation or purification method known in the art such as neutralization and distillation. It is expected that unreacted HCFC-244bb could be recycled, completely or partially, to improve the overall yield of the desired $CF_3CF=CH_2$ (HFO-1234yf). Optionally but preferably, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

In an alternate embodiment of the invention, dehydrohalogenation of HCFC-244bb can also be accomplished by reacting it with a strong caustic solution that includes, but is not limited to KOH, NaOH, $Ca(OH)_2$ and CaO at an elevated temperature. In this case, the strength of the caustic solution is of from about 2 wt % to about 100 wt %, more preferably from about 5 wt % to about 90 wt % and most preferably from about 10 wt % to about 80 wt %. The caustic to HCFC-244bb mole ratio preferably ranges from about 1:1 to about 2:1; more preferably from about 1.1:1 to about 1.5:1 and most preferably from about 1.2:1 to about 1.4:1. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr (0.0966 psig) to about 760 torr (14.69 psig). In addition, a solvent or phase transfer catalyst such as Aliquat 336 may optionally be used to help dissolve the organic compounds in the caustic solution. This optional step may be conducted using solvents that are well known in the art for said purpose. Thereafter, HFO-1234yf may be recovered from the reaction product mixture comprised of unreacted starting materials and by-products by any means known in the art, such as by extraction and preferably distillation. The mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 200 psig and most preferably less than 150 psig. The pressure of the distillation column inherently determines the distillation operating temperature. Preferably in such dehydrofluorination embodiments as described in this section, the conversion HCFC-244bb is at least about 60%, more preferably at least about 75%, and even more preferably at least about 90%. Preferably in such embodiments, the selectivity to HFO-1234yf, is at least about 70%, more preferably at least about 85% and more preferably at least about 95%.

The following non-limiting examples serve to illustrate the invention.

EXAMPLE 1

A continuous liquid phase fluorination of the 2-chloro-3,3,3-trifluoropropene (HCFC-1233xf)+HF→2-chloro-1,1,1,2-tetrafluoropropane (HCFC-244bb) in demonstrated while continuously feeding HCl. The fluorination catalyst for the experiment is $SbCl_5$.

6500 grams of $SbCl_5$ are contained in a Teflon™-lined liquid phase reactor (Teflon is a trademark of E.I. duPont de Nemours & Co) equipped with a catalyst stripper, 2-inch ID (inside diameter) packed column and with a condenser whose function is to return entrained catalyst, some of the unreacted HF and some of the unreacted HCFO-1233xf to the reactor when the system is running in continuous reaction mode. The reactor is 2.75-inch ID×36-inch L (length) and is not equipped with a mixer/agitator. The reactor is heated to about 85° C.-87° C. The catalyst is then activated by the addition of 1500 grams of HF followed by 1500 grams of $Cl_2$. HCl generated by the fluorination of the catalyst raises the reaction system pressure to about 100 psig where it is controlled. The continuous gaseous HF feed is started first. It is bubbled into the liquid catalyst through a dip tube at a rate of 1.1 lb/hr, and when 1.0 lbs of HF has been added, the gaseous HCl and 2-chloro-3,3,3-trifluoropropene feeds are started. They also enter the liquid catalyst by way of a dip tube. The HCl and HCFO-1233xf are fed continuously at rates of 0.56 lb/hr and 1.0 lb/hr respectively. The mole ratio of HF to 1233xf is 7.1:1 and the mole ratio of HCl to 1233xf is 2:1. The reaction temperature is maintained at 85° C.-87° C. and the pressure is maintained at 100 psig. The HCl is gaseous at these conditions and is inert (i.e. does not react). As it bubbles into the liquid reaction mixture it dramatically increases mixing and because of high vapor pressure it helps to maintain the reactor pressure. It exits the reaction system through the top of the catalyst stripper helping to carry out the reaction product, HCFC-244bb with it. The experiment is run continuously for 50 hours. The average conversion of HCFO-1233xf for the run is >99% and the selectivity to 244bb reaches 98%.

EXAMPLE 2

The stream exiting the top of the catalyst stripper in Example 1 containing mainly HCFC-244bb, unreacted HF, and HCl is fed to a conventional distillation column where HCl is recovered and/or recycled back to the liquid phase reactor to aid in mixing, pressure maintenance, and product carrier.

EXAMPLE 3

A 2000 gallon commercial scale reactor is charged with antimony pentachloride catalyst. HCFO-1233xf and HF are fed continuously to the reactor vessel. HF is fed in excess. Hydrogen chloride is added as an additional component to aid mixing and to aid in volatilizing the product. HCFC-244bb, HF and hydrogen chloride exit the vessel and are recovered.

EXAMPLE 4

This example illustrates the continuous vapor phase fluorination reaction of 1,1,2,3-tetrachloropropene (TCP)+ 3HF→2-chloro-3,3,3-trifluoropropene (HCFO-1233xf)+ 3HCl. The fluorination catalyst for the experiment was fluorinated $Cr_2O_3$.

A continuous vapor phase fluorination reaction system consisting of N2, HF, and organic feed systems, feed vaporizer, superheater. 4" ID Monel reactor, acid scrubber, drier, and product collection system was used to study the reaction. The reactor was loaded with 9415.2 grams of pretreated $Cr_2O_3$ catalyst which equates to about 6.5 liters of catalyst. The reactor was then heated to a reaction temperature of about 235° C. with a N2 purge going over the catalyst after the reactor had been installed in a constant temperature sand bath. The reactor was at about 3 psig of pressure. HF feed was introduced to the reactor (via the vaporizer and superheater) as a co-feed with the N2 for 15 minutes when the N2 flow was stopped. The HF flow rate was adjusted to 1.4 lb/hr and then 1,1,2,3-tetrachloropropene (TCP) feed was started to the reactor (via the vaporizer and superheater). The feed rate of TCP was kept steady at about 0.8 lb/hr and HF feed was kept steady at 1.4 lb/hr for about a 15 to 1 mole ratio of HF to TCP.

Once the reaction started the catalyst bed temperature rose to a range of 250-260° C. The contact time at 250-260° C., 3 psig and the above feed rates was calculated to be about 16 s. The average composition of the material that was collected over 500 hours of on-stream time was about 97.2 GC area % HCFO-1233xf, 1.6 GC area % 244bb, 0.6 GC area % HFO-1234yf/HFC-245cb, 0.1 GC area % HCFC-1223xd, and 0.08 GC area % HCFO-1231xf. After 500 hours an under fluorinated intermediate, 2,3-dichloro-3,3-difluoropropene (HCFO-1232xf) started to appear as the selectivity to HCFO-1233xf decreased when the catalyst started losing activity. When the selectivity to HCFO-1233xf decreased to about 83% after 650 hours of on-stream time the reaction was stopped due to loss of catalyst activity. The conversion of TCP remained at >99% throughout the run.

EXAMPLE 5

The reactor effluent from the reaction described in Example 4 is fed to a conventional distillation column where HCl distillate is recovered. The distillation column bottoms mainly contains unreacted HF and HCFO-1233xf and are fed forward for additional processing/purification. The HCl that is recovered, in whole or in part, is then used as the source of the co-fed HCl, to the liquid phase reaction system as described in Example 1.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the production of 2,3,3,3-tetrafluoropropene which comprises:
    (i) continuously reacting 2-chloro-3,3,3,-trifluoropropene with hydrogen fluoride, in a liquid phase reaction and co-feeding hydrogen chloride, in the presence of a liquid phase fluorination catalyst to produce a composition comprising 2-chloro-1,1,1,2-tetrafluoropropane, wherein the hydrogen chloride is added into the reaction from an external source at a pressure of about 100 psig or more;
    (ii) dehydrohalogenating the 2-chloro-1,1,1,2-tetrafluoropropane under conditions effective to produce 2,3,3,3-tetrafluoropropene; wherein
    (iii) said 2-chloro-3,3,3,-trifluoropropene is produced by a process comprising fluorinating 1,1,2,3-tetrachloropropene with hydrogen fluoride to produce an intermediate product comprising hydrogen fluoride, 2-chloro-3,3,3,-trifluoropropene and hydrogen chloride;
    (iv) removing from said intermediate product at least a portion of said hydrogen chloride;
    and (v) introducing at least a portion of the hydrogen chloride removed in said step (iv) into said liquid phase reaction of step (i).

2. The process of claim 1 wherein the reacting of step (i) is conducted in a liquid phase reaction vessel.

3. The process of claim 1 wherein the dehydrohalogenating reacting of step (ii) is conducted continuously.

4. The process of claim 1 wherein the mole ratio of hydrogen fluoride to 2-chloro-3,3,3-trifluoropropene fed to the reaction of step (i) is from about 1:1 to about 50:1.

5. The process of claim 1 wherein the mole ratio of hydrogen chloride to 2-choro-3,3,3-trifluoropropene fed to the reaction of step (i) is from about 0.1:1 to about 10:1.

6. The process of claim 1 wherein the liquid phase fluorination catalyst comprises $SbCl_5$, $SbCl_3$, $SbF_5$, $SnCl_4$, $TaCl_5$, $TiCl_4$, $NbCl_5$, $MoCl_6$, $FeCl_3$, $CrF_3$, $Cr2O3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, a fluorinated species of $Cr_2O_3$, or combinations thereof.

7. The process of claim 1 wherein the reacting of step (i) is conducted at a temperature of from about 30° C. to about 200° C.

8. The process of claim 1 wherein the reacting of step (i) is conducted at a pressure of up to about 200 psia.

\* \* \* \* \*